US00PP12625P2

(12) United States Plant Patent
Duncan

(10) Patent No.: US PP12,625 P2
(45) Date of Patent: May 14, 2002

(54) SEASHORE PASPALUM PLANT 'SEA ISLE 2000'

(75) Inventor: Ronny R. Duncan, Griffin, GA (US)

(73) Assignee: University of Georgia Research Foundation, Athens, GA (US)

( * ) Notice: Subject to any disclaimer, the term of this patent is extended or adjusted under 35 U.S.C. 154(b) by 0 days.

(21) Appl. No.: 09/552,104

(22) Filed: Apr. 19, 2000

(51) Int. Cl.[7] ..... A01H 5/00
(52) U.S. Cl. ..... Plt./388
(58) Field of Search ..... Plt./388

*Primary Examiner*—Bruce R. Campell
*Assistant Examiner*—Annette H. Para
(74) *Attorney, Agent, or Firm*—Needle & Rosenberg, P.C.

(57) ABSTRACT

A vegetatively reproduced seashore paspalum cultivar, selected as a mutation from the cultivar Adalayd®, is named 'SEA ISLE 2000'. It is distinguished by high tolerance to salinity, dark green color, extremely fine leaf blades that are generally ≦1.5 mm in width, and the ability to tolerate mowing to 5/32 inch height. These distinguishing characteristics make 'SEA ISLE 2000' particularly suitable as a turfgrass for lawns and golf courses, especially golf course greens.

3 Drawing Sheets

SUMMARY OF THE INVENTION

The present invention comprises a new and distinct plant of *Paspalum vaginatum* O. Swartz, which has been given the name 'SEA ISLE 2000'. The following traits have been repeatedly observed and are the most pronounced characteristics of this new cultivar when grown in Georgia, and in combination, they distinguish it from Adalayd®, the most closely related variety:

1. High tolerance to salinity.
2. Dark green color and extremely fine blades (≦1.5 mm in width)
3. Can tolerate mowing to 5/32 inch height.

BRIEF DESCRIPTION OF THE FIGURES

FIG. 1 shows a typical specimen of 'SEA ISLE 2000' with the inflorescences (commonly referred to as spikes) highlighted against a white paper background.

FIG. 2 shows two rows, each containing examples of young inflorescences (commonly referred to as spikes) and sheaths (with leaf blades trimmed) of 'SEA ISLE 2000'.

FIG. 3 shows SEA ISLE 2000 after planting and mowing. SEA ISLE 2000's dark green color, extremely fine blades and tolerance to close mowing are shown.

DETAILED DESCRIPTION

Background of the Invention

*Paspalum vaginatum* O. Swartz is a grass in the Panicoideae subfamily which inherently colonizes saline ecosystems, e.g. along sea coasts and on brackish sands. Commonly referred to as "seashore paspalum", it is an ecologically aggressive, littoral warm-season perennial grass species. It is both rhizomatous and stoloniferous. Because it can tolerate waterlogged conditions and periodic, meso-saline flooding, it has been useful for erosion control on salinity-sensitive lands and areas subjected to tidal influences, e.g. for beach preservation. The grass occurs in the wild in both hemispheres. In the Americas, it is found naturally almost exclusively along the Atlantic coastline in marshy, brackish ecosystems. In Australia, it is found in tropical heaths, tropical and subtropical rainforests, semi-arid shrub woodlands, acacia shrublands, and mangrove swamps.

Generally, *P. vaginatum* is a self-incompatible, diploid species. The diploid chromosome number recognized for the species is 20, and the genome of this species is the "D" genome. It has a $C_4$ method of carbon fixation, using the NADP-ME pathway, which is characteristic for grasses that occur in moist ecosystems.

*P. vaginatum* has been introduced into salt-affected areas as the need for forages, land reclamation and turf have increased. The variety Adalayd® has been widely used in Australia as a lawngrass, although its use on bowling greens was curtailed when superdwarf bermuda grasses were introduced to the country. *P. vaginatum* was identified on a marsh golf course at the Sea Island Golf Club in the southeastern United States, where the grass was already established along the golf course fairways when the course was built. *P. vaginatum* was introduced sporadically throughout the 1970s and 1980s for golf course fairways and home lawn use, and one variety from Australia became reasonably well-known in the United States, Adalayd® (U.S. Plant Pat. No. 3,939). However, this variety was not managed effectively in the United States, and the lack of optimization of fertilization regimes and irrigation requirements led to disenchantment about its performance. With the introduction of the dwarf bermudagrasses and other warm season grasses, the use of a seashore paspalum variety as a turfgrass has been minimal. In the late 1980s a variety of seashore paspalum was introduced to the fairways of a golf course in Honolulu, Hi., and is now referred to as 'Salam' (an unpatented variety).

With increasing pressures on golf course developers to use coastal venues and reclaimed water sources (or brackish water), there is a need for a high-quality seashore paspalum turfgrass not only for use on the fairways, but one that is specifically adapted for use on golf course greens, where it is subjected to extreme mowing and foot traffic stress. Prior to the selection and cultivation of SEA ISLE 2000, no seashore paspalum has ever been developed specifically for use on golf course greens.

Origin of the Invention

SEA ISLE 2000 is a selection based on an observation of a darker green patch in a seashore paspalum green at a golf course in Florida. The golf course was sprigged with the seashore paspalum Adalayd® twelve years prior to the selection of SEA ISLE 2000. Thus, SEA ISLE 2000 is a mutation, or "sport", derived from Adalayd®.

Propagation

SEA ISLE 2000 can be propagated asexually through sprigs or sod. To maintain purity and minimize cross-contamination in plots, single stolons of SEA ISLE 2000 are initially planted in soilless media, then continually increased in the greenhouse until ready for field planting on golf courses or sports fields. Foundation fields are planted from the greenhouse grown material. Asexual reproduction demonstrates that the unique features of 'SEA ISLE 2000' are stable and are reproduced true-to-type in subsequent generations. SEA ISLE 2000 was asexually propagated at the Georgia Agricultural Experiment Station, College of Agricultural and Environmental Sciences, Department of Soil and Crop Sciences, Griffin, Ga. U.S.A.

SEA ISLE 2000 can also be propagated through in vitro tissue culturing (see Cordona and Duncan, 1997, Crop Science 37:1297–1302).

Botanical Description:

*Culms*.—The flowering culms are erect or basally decumbent, ranging in height from 8–10 cm (unmowed) with 5–6 glabrous nodes.

*Leaves*.—Medi-culm leaves are fine-textured, do not have sheath or blade auricles, and are distichous. The blades are 50 mm long, approximately 0.5–1.5 mm wide, linear and glabrous, tapering to a narrow apex. The prophyllum is 20 mm long. The 1 mm ligule is membraneous and truncate with a pubescent collar. The leaf color, based on The Royal Horticultural Society Colour Chart, is 137A. The leaf edges are smooth and the leaf veins are obscure.

*Stolons*.—Nodes are pubescent, and the internode length is 5 mm.

*Inflorescence*.—The inflorescence is composed of two primary racemes, 20 mm in length, with 16–20 twin-rowed spikelets on each primary raceme, and is fully exserted at maturity. Each spikelet is solitary, plano-convex, subsessile, elliptic, 2.5 mm long, and 0.9–1.5 mm wide. Anthers are 1.2–1.3 mm long. The glumes are glaborous.

*Seed*.—Rarely produced, but are typically 2.5 mm long and 1.5 mm wide, narrowly obovate, subacute, and slightly concavo-convex. The seed is straw-colored when mature.

ADDITIONAL DESCRIPTION

Salt Tolerance and Growth Rates

SEA ISLE 2000 was compared to the variety Adalayd® in a standard laboratory salinity stress study. As shown in Table 1, SEA ISLE 2000 was consistently more tolerant of salt, both in terms of its growth at a relatively high salt concentration (40 deciSiemens per meter, or $dSm^{-1}$) as well as in the amount of salinity required (EC) to result in a 25% reduction in growth. In addition, SEA ISLE 2000 is more aggressive in its overall growth rate in the absence of salt.

TABLE 1

| | Growth (g/container[a]) | | | | EC@25% growth reduction $dSm^{-1}$ | |
|---|---|---|---|---|---|---|
| | No Salt | | 40 $dSm^{-1}$ | | | |
| | Shoot | Root | Shoot | Root | Shoot | Root |
| Adalayd ® | 0.23 | 0.20 | 0.08 | 0.13 | 7.64 | 15.79 |
| SEA ISLE 2000 | 0.61+ | 0.40* | 0.26* | 0.36** | 13.88 | 18.60 |
| F test | *** | *** | *** | *** | 0.38 | 0.38 |
| | Crown Total | | Crown Total | | | |
| Adalayd ® | 0.57 | 1.00 | 0.37 | 0.59 | | |
| SEA ISLE 2000 | 0.82 | 1.82* | 0.75** | 1.36* | | |
| F test | *** | *** | *** | *** | | |

*, , *, + = 0.001, 0.01, 0.05, and 0.1 probability levels, respectively (Dunnett T Test, Steel & Torrie, 1960, Principles and Procedures of Statistics, McGraw-Hill, New York)
[a]5 cm top diameter × 20 cm depth = container

Leaf Color

The color of turfgrasses can vary significantly depending on environmental conditions. When compared side-by-side, the following Royal Horticultural Society Colour Chart values are obtained for SEA ISLE 2000 and Adalayd®:

SEA ISLE 2000: 137A.
Adalayd®: 138A.

Leaf Color

No seashore paspalum variety has ever been mowed to the extremely short lengths demanded by golf course on 'superintendents for acceptable greens. The following data were collected SEA ISLE 2000 ',during a two year study in which the plots were kept mowed to 5/32 inch twice a week and subjected to traffic, using machines to simulate excess wear or compaction. There were two independent studies; and each study had four replications. The scale for Table 1 is from 1–9, with 9 being the ideal quality, color and density. On this scale, a rating >6.5 is acceptable for golf green use. The turf quality rating is a visual rating based on cosmetic appearance, color, leaf texture, denseness of canopy and uniformity of stand. Adalayd®, which has been observed for many years on courses in the United States, does not perform nearly as well as SEA ISLE 2000 in terms of turf quality parameters, having an overall rating of only 5.0.

TABLE 2

Turf Quality, Color and Density of SEA ISLE 2000 during the traffic studies and as a f(N:K) treatments

| Treatment | Quality | | Color | | Density | |
|---|---|---|---|---|---|---|
| (N:K kg $ha^{-1}$) | 1 | 2 | 1 | 2 | 1 | 2 |
| 196:92 | 7.5 | 7.1 | 7.8 | 7.4 | 7.9 | 7.6 |
| 196:392 | 7.5 | 7.2 | 7.9 | 7.5 | 7.9 | 7.6 |
| 392:92 | 8.1 | 7.8 | 8.6 | 8.2 | 8.5 | 8.2 |
| 392:392 | 8.1 | 7.7 | 8.5 | 8.1 | 8.5 | 8.1 |
| on a N basis | *** | *** | *** | *** | *** | *** |

TABLE 3

Growth, Density, and Verdure of SEA ISLE 2000 as a f(N:K) treatments and traffic stress. Shoot growth was measured 6 days after traffic stress. Shoot density and verdure were measured 6 or 9 days after traffic stress.

| Treatment | Shoot growth ($kg\ ha^{-1}$) | | Shoot Density ($g\ dm^2$) | | Verdure | |
|---|---|---|---|---|---|---|
| (N:K $kg\ ha^{-1}$) | 1 | 2 | 1 | 2 | 1 | 2 |
| 196:92 | 3.99 | 4.68 | 48.3 | 50.5 | 0.42 | 0.36 |
| 196:392 | 4.97 | 6.34 | 50.8 | 48.6 | 0.45 | 0.36 |
| 392:92 | 6.31 | 5.47 | 50.1 | 53.1 | 0.57 | 0.27 |
| 392:392 | 7.85 | 6.86 | 56.8 | 54.6 | 0.51 | 0.29 |
| Traffic vs. | $6.25^{ns}$ | $5.66^{ns}$ | $50.6^{ns}$ | $49.1^{ns}$ | 0.39* | 0.28* |
| Non-Traffic | 5.41 | 5.90 | 55.5 | 54.3 | 0.59 | 0.36 |

*, , *, 0.0001, 0.01, 0.05 level of probability; ns = nonsignificant

Disease Resistance

SEA ISLE 2000 has good resistance to dollar spot, and mole cricket resistance that is comparable to that of Adalayd®.

What is claimed:

1. A new and distinct plant of *Paspalum vaginatum* as herein shown and described, that is characterized by a unique combination of high tolerance to salinity, dark green color, fine leaf blade (≦1.5 mm in width), and excellent tolerance to extremely close mowing (5/32 inch height).

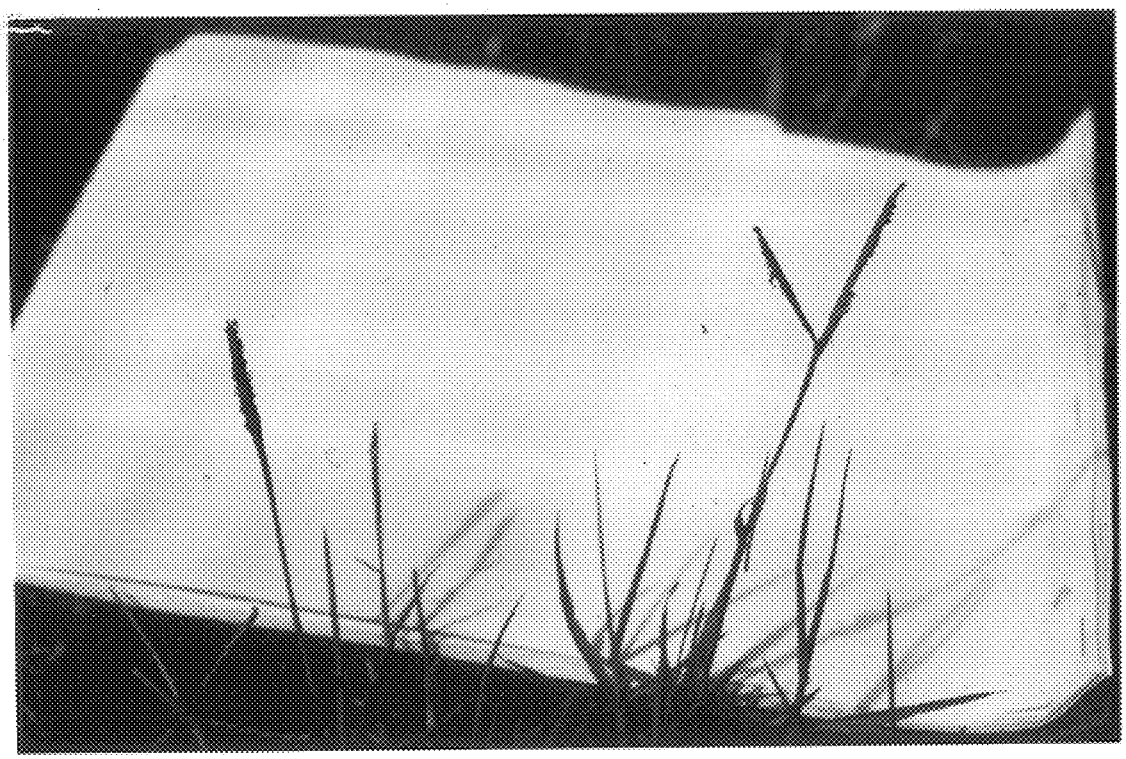

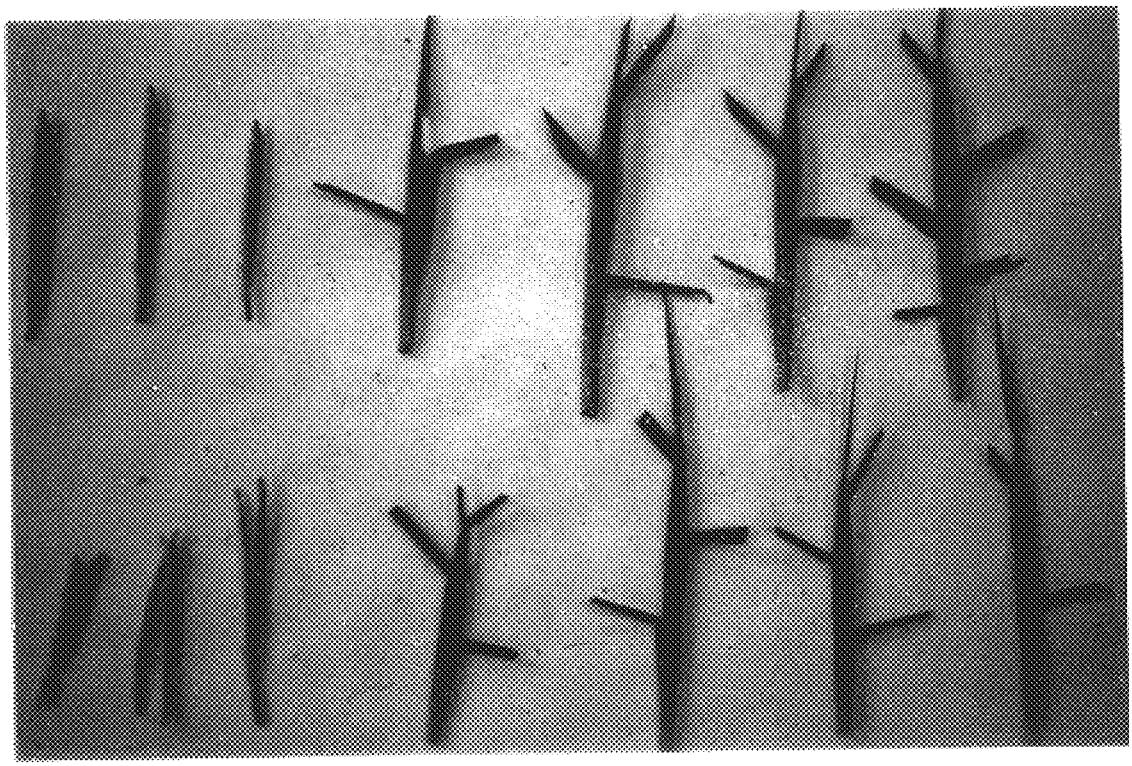

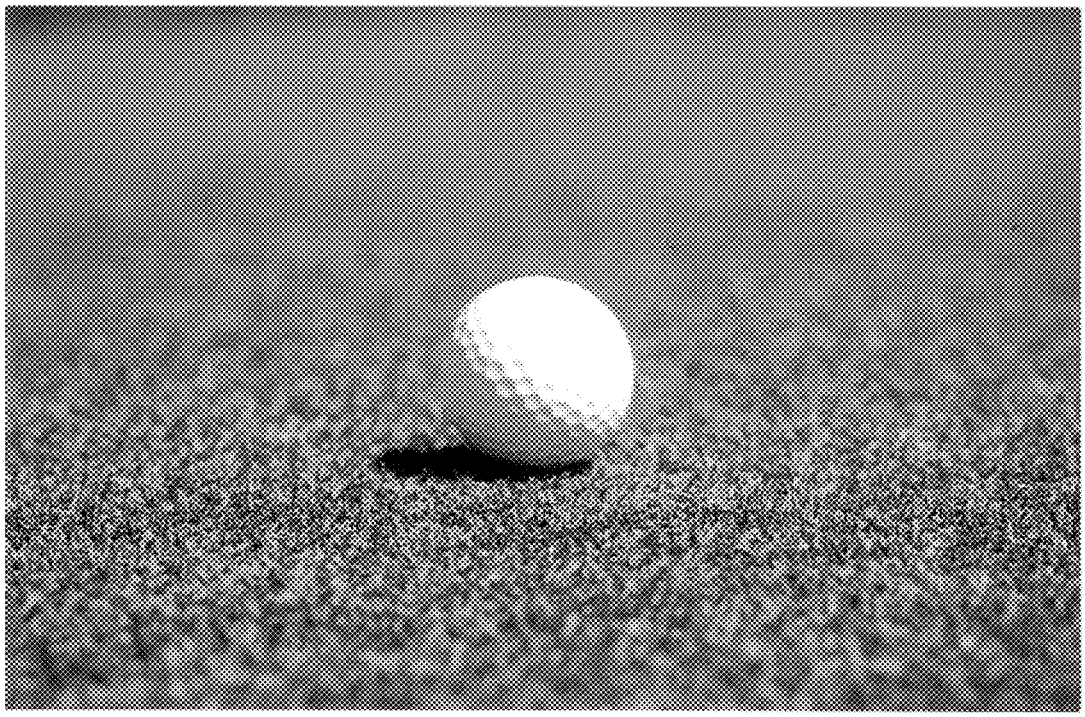

* * * * *